United States Patent (10) Patent No.: US 8,114,640 B2
Sherman et al. (45) Date of Patent: Feb. 14, 2012

(54) MACROCYCLIZATION OF COMPOUNDS FROM SOLID SUPPORT USING THIOESTERASES

(75) Inventors: David H. Sherman, Ann Arbor, MI (US); Wolfgang Seufert, Ann Arbor, MI (US); Zachary Q. Beck, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 349 days.

(21) Appl. No.: 12/261,768

(22) Filed: Oct. 30, 2008

(65) Prior Publication Data

US 2009/0111152 A1 Apr. 30, 2009

Related U.S. Application Data

(60) Provisional application No. 60/983,622, filed on Oct. 30, 2007.

(51) Int. Cl.
*C12P 17/14* (2006.01)
*C12P 17/10* (2006.01)
*C12N 9/00* (2006.01)
*C12N 9/16* (2006.01)
*C12N 1/20* (2006.01)
*C12N 15/00* (2006.01)
*C07H 21/04* (2006.01)

(52) U.S. Cl. ........ 435/120; 435/121; 435/183; 435/196; 435/252.3; 435/320.1; 536/23.2

(58) Field of Classification Search .................. None
See application file for complete search history.

(56) References Cited

U.S. PATENT DOCUMENTS

2007/0184516 A1 8/2007 Marahiel et al.

OTHER PUBLICATIONS

Akey et al., Structural basis for macrolactonization by the pikromycin thioesterase. *Nat. Chem. Biol.* 2(10): 537-42 (2006).
Backes et al., Activation method to prepare a highly reactive acylsulfonamide "Safety-Catch" linker for solid-phase synthesis. *J. Am. Chem. Soc.* 118: 3055-6 (1996).
Backes et al., An alkanesulfonamide "Safety-Catch" linker for solid-phase synthesis. *J. Org. Chem.* 64: 2322-30 (1999).
Beck et al., Chemoenzymatic synthesis of cryptophycin/arenastatin natural products. *Biochemistry*, 44: 13457-66 (2005).
Buchholz et al., Structural basis for binding specificity between subclasses of modular polyketide synthase docking domains. *ACS Chem. Biol.* 4(1): 41-52 (2009).
Cane et al., Harnessing the biosynthetic code: combinations, permutations, and mutations. *Science*, 282: 63-8 (1998).
Eggen et al., The cryptophycins: their synthesis and anticancer activity. *Med. Res. Rev.*, 22: 85-101 (2002).

Eggen et al., Total synthesis of cryptophycin-24 (Arenastatin A) amenable to structural modifications in the C16 side chain. *J. Org. Chem.* 65: 7792-9 (2000).
Eissler et al., The synthesis of cryptophycins. *Synthesis*, 22: 3747-89 (2006).
Golakoti et al., Total structures of cryptophycins, potent antitumor depsipeptides from the blue-green alga nostoc sp. strain GSV 224. *J. Am. Chem. Soc.* 116: 4729-37 (1994).
Golakoti et al., Structure determination, conformational analysis, chemical stability studies, and antitumor evaluation of the cryptophycins. Isolation of 18 new analogs from Nostoc sp. strain GSV 224. *J. Am. Chem. Soc.* 117: 12030-49 (1995).
Kittendorf et al., Interrogating the molecular basis for multiple macrolactone ring formation by the pikromycin polyketide synthase. *Chem. Biol.* 14(8): 944-54 (2007).
Kohli et al., Biomimetic synthesis and optimization of cyclic peptide antibiotics. *Nature*, 418: 658-61 (2002).
Kotoku et al., Synthesis of 15,20-triamide analogue with polar substituent on the phenyl ring of arenastatin A, an extremely potent cytotoxic spongean depsipeptide. *Bioorg. Med. Chem.* 14: 7446-57 (2006).
Lessmann et al., Enantioselective synthesis on the solid phase. *Chem. Commun. (Camb)*, 28: 3380-9 (2006).
Liang et al., Cryptophycins-309, 249 and other cryptophycin analogs: preclinical efficacy studies with mouse and human tumors. *Invest. New Drugs*, 23: 213-24 (2005).
Magarvey et al., Biosynthetic characterization and chemoenzymatic assembly of the cryptophycins. Potent anticancer agents from cyanobionts. *ACS Chem. Biol.* 1:766-79 (2006).
Marahiel et al., Modular peptide synthetases involved in nonribosomal peptide synthesis. *Chem. Rev.* 97:2651-4 (1997).
Meldal et al., A PEGA resin for use in the solid-phase chemical—enzymatic synthesis of glycopeptides. *J. Chem. Soc. Chem. Commun.* 1849-50 (1994).
Meldal, Pega: a flow stable polyethylene glycol dimethyl acrylamide copolymer for solid phase synthesis. *Tetrahedron Lett.* 33: 3077-80 (1992).
Murakami et al., Synthesis of amide analogs of Arenastatin A. *Tetrahedron*, 56:9121-8 (2000).
Nicolaou et al., Solid- and solution-phase synthesis of vancomycin and vancomycin analogues with activity against vancomycin-resistant bacteria. *Chemistry*, 7:3798-823 (2001).
Obrecht et al., A novel and efficient approach for the combinatorial synthesis of Structurally diverse pyrimidines on solid support. *Helv. Chim. Acta*, 80:65-72 (1997).
Patek et al., "Safety-catch anchoring linkage for synthesis of peptide amides by Boc/Fmoc strategy", *Tetrahedron Lett.*, 32:3891-4 (1991).
Paterson et al., "A combinatorial approach to polyketide-type libraries by iterative asymmetric aldol reactions performed on solid support", *Angew. Chem. Int. Ed. Engl.*, 39:3315-9 (2000).
Routledge et al., "The use of a dithiane protected benzoin photolabile safety catch linker for solid-phase synthesis", *Tetrahedron Lett.*, 38:1227-1230 (1997).
Schwartz et al., "Pharmaceuticals from cultured algae", *J. Ind. Microbiol.*, 5:113-23 (1990).
Smith et al., "Cryptophycin: a new antimicrotubule agent active against drug-resistant cells", *Cancer Res.*, 54:3770-84 (1997).

(Continued)

*Primary Examiner* — Christian Fronda
(74) *Attorney, Agent, or Firm* — Marshall, Gerstein & Borun LLP

(57) ABSTRACT

A method of preparing macrocycles using solid support chemistry and thioesterases is disclosed. Also disclosed are novel macrocycles.

14 Claims, No Drawings

OTHER PUBLICATIONS

Tamaki et al., "Biomimetic formation of gramicidin S by dimerization—cyclization of pentapeptide precursor on solid support", *Tetrahedron Lett.*, 47:8475-8 (2006).

Umarye et al., "Biology-oriented synthesis of stereochemically diverse natural-product-derived compound collections by iterative allylations on a solid support", *Chemistry*, 13:3305-19 (2007).

Wu et al., "Biomimetic synthesis of gramicidin s and analogues by enzymatic cyclization of linear precursors on solid support", *Org. Lett*, 5:1749-52 (2003).

Wuts, *Greene's Protective Groups in Organic Synthesis*, 2nd ed., New York: John Wiley & Sons, (1991).

International Search Report, Korean Patent Office, PCT/US2008/81786, dated Jun. 30, 2009.

MACROCYCLIZATION OF COMPOUNDS FROM SOLID SUPPORT USING THIOESTERASES

CROSS-REFERENCE TO RELATED APPLICATIONS

This application claims priority to U.S. Provisional Application No. 60/983,622, filed Oct. 30, 2007, the disclosure of which is incorporated by reference in its entirety.

STATEMENT OF GOVERNMENT SUPPORT

This invention was made with U.S. government support under National Institutes of Health Grant No. RO1 CA108874. The government has certain rights in this invention.

BACKGROUND

Many natural products of pharmacological importance have macrocyclic structures, like the polyketide antibiotic erythromycin, the non-ribosomal peptide cyclosporine or the cryptophycins, a family of depsipeptides and potent antitumor agents. In nature, these macrocyclic compounds are synthesized by modular enzymatic 'assembly lines' using polyketide (PK) synthases, non-ribosomal peptide (NRP) synthetases or hybrid NRP/PK synthetases. (See, e.g., Cane, et al., *Science*, 282:63-68 (1998); Marahiel, et al., *Chem. Rev.*, 97:2651-2674 (1997)). During biosynthesis, the intermediates are bound to the enzymes by a thioester, and, in the final step, are cyclized by an integrated carboxy-terminal thioesterase (TE) domain.

Previous strategies for the synthesis and enzyme catalyzed on-resin cyclization of peptides involved substrates bound via ester or thioester linkage to a solid support. (See, Kohli, et al., *Nature*, 418:658-661 (2002); Wu, et al., *Org. Lett.*, 5:1749-1752 (2003); Tamaki, et al., *Tetrahedron Lett.*, 47:8475-8478 (2006)). Solid-phase synthesis of linear polyketides that employ diverse reaction conditions have been reported. (See, Umarye, et al., *Chem. Eur. J.*, 13:3305-3319 (2007); Lessmann, et al., *Chem. Commun.*, 3380-3389 (2006); Paterson, et al., *Angew. Chem. Int. Ed.*, 39:3315-3319 (2000)). To facilitate the synthesis of large libraries of macrocyclic compounds, a method that enables direct release and cyclization of compounds on-resin is required.

Cryptophycins, a class of macrocyclic depsipeptides, were first isolated in the 1990s from *Nostoc* sp. ATCC 53789 and *Nostoc* sp. GSV 224. (See, Schwartz, et al., *J. Ind. Microbiol.*, 5:113-123 (1990); Golakoti, et al., *J. Am. Chem. Soc.*, 116: 4729-4737 (1994); Golakoti, et al., *J. Am. Chem. Soc.*, 117: 12030-12049 (1995).) The therapeutic potential of these natural products is derived from their potent and highly selective cytotoxicity, including multi-drug-resistant tumor cell lines. The biological properties generated significant interest in their large-scale isolation, total synthesis and modification. (Smith, et al., *Cancer Res.*, 54:3779-3784 (1994).) Currently, more than 25 naturally occurring cryptophycins, and several hundred synthetic analogs, have been described. Several of these analogs have been identified as advanced anti-cancer therapeutic leads that are being considered for clinical evaluation. (See, Liang, et al., *Invest. New Drugs*, 23(3):213-24 (2005).) Most natural cryptophycins consist of four hydroxy or amino acids (units A-D, respectively): δ-hydroxy phenyloctenoic acid, 3-chloro-O-methyl-D-tyrosine, (R)-α-methyl-β-alanine (or β-alanine) and L-leucic acid (Scheme 1). (See., e.g., Eissler, et al., *Synthesis*, 3747-3789 (2006); and Eggen, et al., *Med. Res. Rev.*, 22:85-101 (2002).)

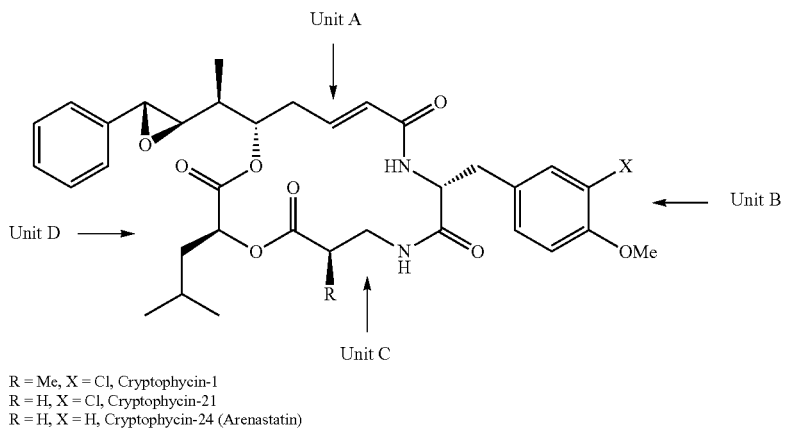

R = Me, X = Cl, Cryptophycin-1
R = H, X = Cl, Cryptophycin-21
R = H, X = H, Cryptophycin-24 (Arenastatin)

Recently, the gene cluster responsible for production of cryptophycins was characterized from the cyanobacteria *Nostoc* sp. ATCC 53789 and *Nostoc* sp. GSV 224. (See Magarvey, et al., *ACS Chem. Biol.*, 1:766-779 (2006).) Furthermore, specific enzymes involved in their biosynthesis have been heterologously expressed, purified and characterized including the cryptophycin thioesterase (Crp TE), which is responsible for the macrolactonization of the linear intermediate. (See, e.g., Magarvey, et al., *ACS Chem. Biol.*, 1:766-779 (2006).)

A need exists to prepare macrocyclic compounds, like cryptophycins, in a manner that employs the benefits of solid support chemistry (e.g., adaptability and easy modification) and limits undesired side reactions, such as elimination byproducts. This disclosure describes the solid-phase synthesis and on-resin cyclization of crytophycin analogs and general methods for forming macrocycles using solid support chemistry.

SUMMARY

Disclosed herein are methods of preparing macrocycles using solid support chemistry. Specifically, methods are disclosed for preparing macrocycles using a safety-catch linker on solid support. Also disclosed herein are cryptophycin derivatives and methods of preparing them using solid support.

Thus, one aspect disclosed herein is a process of preparing a macrocyclic compound by admixing a thioesterase and an intermediate compound to form the macrocyclic compound. The intermediate compound is attached to a safety catch linker via an amide functional group and the safety catch linker, in turn, is attached to a solid support. The intermediate compound further has a nucleophilic functional group that is separated from the amide functional group via a linear backbone.

Another aspect disclosed herein is a process of preparing a compound of formula (II) comprising admixing a compound of formula (I) and a thioesterase to form the compound of formula (II),

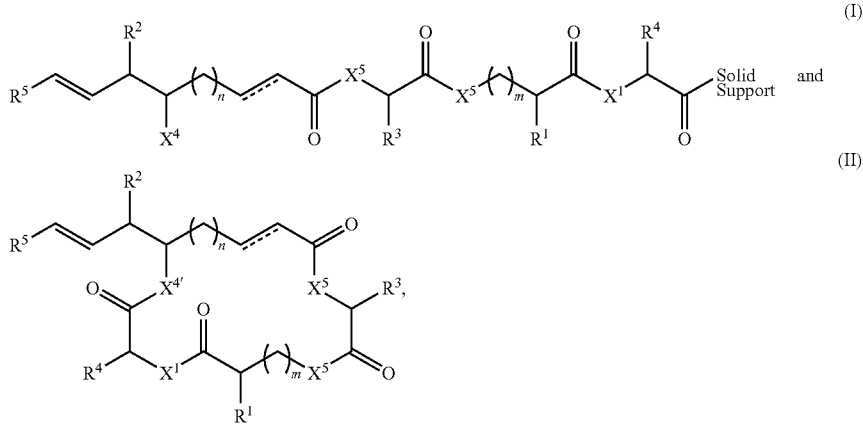

(I)

(II)

wherein $X^1$ is selected from the group consisting of O, NH, and S; $X^4$ is selected from the group consisting of OH, $NH_2$, and SH; $X^{4'}$ is selected from the group consisting of O, NH, and S; $X^5$ is independently selected from the group consisting of O, S, NH, and $CR^6$; $R^2$ and $R^6$ are each independently selected from the group consisting of hydrogen and $C_{1-6}$alkyl; $R^1$, $R^3$, and $R^4$ are each independently selected from the group consisting of hydrogen, $C_{1-6}$alkyl, $C_{1-6}$alkylenearyl, $C_{1-6}$alkyleneheteroaryl, hydroxy$C_{1-6}$alkyl, thio$C_{1-6}$alkyl, $C_{1-6}$alkyleneCO$_2$H, $C_{1-6}$alkyleneNH$_2$, $C_{1-6}$alkyleneC(O)NH$_2$, and $C_{1-6}$alkyleneNH(NH)NH$_2$; $R^5$ is selected from the group consisting of aryl, heteroaryl, cycloalkyl, and heterocycloalkyl; a dashed line indicates an optional cis or trans double bond; Solid Support comprises a polymer or glass substrate; n is 1, 2, 3, 4, 5, 6, or 7; and m is 0 or 1. In some embodiments, n or m is 1. In some cases, $R^3$ is $C_{1-6}$alkylenearyl, and aryl is selected from the group consisting of phenyl, 4-hydroxy-3-chlorophenyl, and 4-hydroxyphenyl. In specific cases, $X^1$ is NH or O and $X^5$ is NH and/or $X^4$ is OH and $X^{4'}$ is O. In various cases, $R^5$ is aryl or heteroaryl. In some embodiments, the polymer substrate comprises a polyethylene glycol-acrylamide copolymer. In some specific cases, the polymer substrate further comprises an alkylated acylsulfonamide linker (e.g., a linker of formula —N(CH$_2$CN)SO$_2$(CH$_2$)$_p$CONH— polymer substrate, wherein p is an integer of 1 through 8).

In another aspect, the method disclosed herein is a process for preparing a compound of formula (IV) comprising admixing a compound of formula (III) and cryptophycin thioesterase to form the compound of formula (IV),

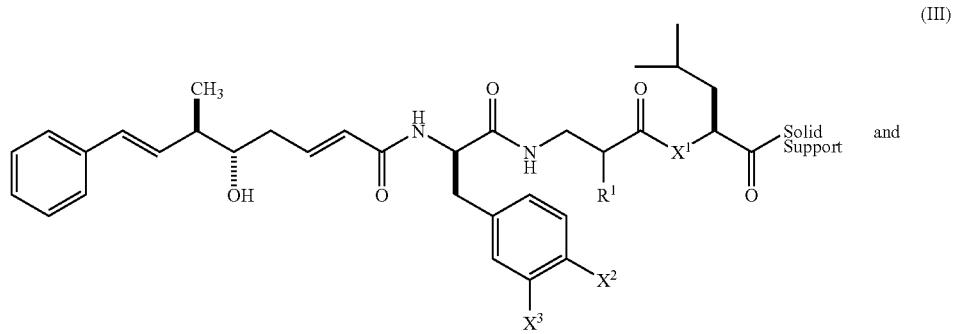

(III)

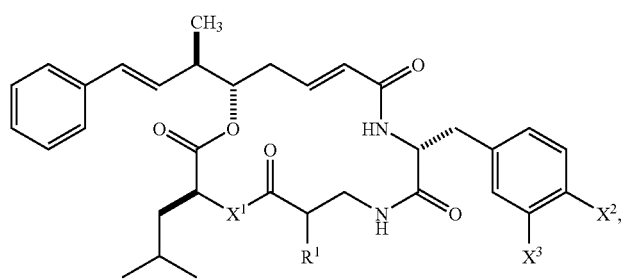

wherein $X^1$ is selected from the group consisting of O, NH, and S; $X^2$ is selected from the group consisting of hydrogen, $OC_{1-6}$alkyl, hydroxyl, and $C_{1-6}$alkyl; $X^3$ is selected from the group consisting of hydrogen, halo, and $C_{1-6}$alkyl; $R^1$ is selected from the group consisting of hydrogen, $C_{1-6}$alkyl, $C_{1-6}$alkylenearyl, $C_{1-6}$alkyleneheteroaryl, hydroxy$C_{1-6}$alkyl, thio$C_{1-6}$alkyl, $C_{1-6}$alkyleneCO$_2$H, $C_{1-6}$alkyleneNH$_2$, $C_{1-6}$alkyleneC(O)NH$_2$, and $C_{1-6}$alkyleneNH(NH)NH$_2$; and Solid Support is a polymer or glass substrate. In some cases, the polymer substrate comprises a polyethylene glycol-acrylamide copolymer. The polymer substrate can further comprise an alkylated acylsulfonamide linker. In some specific cases, $R^1$ is methyl, $X^1$ is NH or O, $X^2$ is methoxy, $X^3$ is chloro, and combinations thereof. In various cases, the Crp TE can have a concentration of about 0.1 μmol to about 0.3 μmol and/or the reaction time can be about 3 hours to about 12 hours.

In one specific case, the process disclosed herein provides the compound of formula (IV) in a ratio to an undesired byproduct compound of formula (V) in a molar ratio of at least 2:1

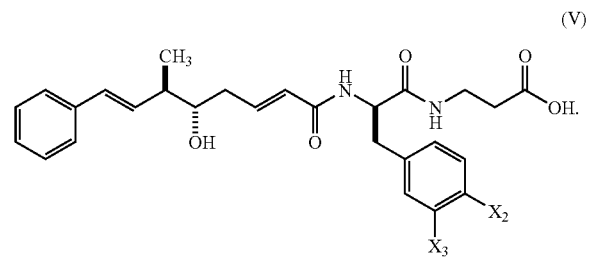

DETAILED DESCRIPTION

Disclosed herein are methods of preparing macrocycles using solid support and thioesterases. A safety-catch linker is used, which is stable to a variety of synthetic conditions and can be selectively removed by specific reaction conditions. Those specific reaction conditions depend upon the particular safety-catch linker used. Also disclosed herein are cryptophycin derivatives and methods of preparing them using solid support.

A macrocyclic compound, as used herein, is a compound having a cyclic structure comprising 14 to 26 atoms in the cyclic structure. The macrocycle can further comprise various substituents on one or more of the atoms that form the cyclic structure. The atoms that form the macrocycle include carbon, and one or more of nitrogen, oxygen, and sulfur.

An intermediate compound, as used herein, is a compound that comprises functional group(s) compatible with a thioesterase such that upon contact with the thioesterase the intermediate compound can form the macrocycle. The intermediate compound is attached to a safety catch linker via an amide bond functional group, and further has a nucleophilic functional group, which is separated from the amide by a linear backbone. The safety catch linker is attached to a solid support.

The nucleophilic functional group is a group that has nucleophilic properties. Examples of nucleophilic functional groups include, but are not limited to, amine, alcohol, and thiol.

The linear backbone can be of at least 12 atoms, at least 14 atoms, at least 16 atoms, at least 18 atoms, or at least 20 atoms. The linear backbone can comprise amino acid residues linked by amide or ester bonds, or synthetic groups, such as alkyl, cycloalkyl, heterocycloalkyl, alkenyl, alkynyl, heteroaryl, or aryl groups, or mixtures thereof.

As used herein, the term "alkyl" refers to straight chained and branched hydrocarbon groups, nonlimiting examples of which include methyl, ethyl, and straight chain and branched propyl and butyl groups. The term "alkyl" includes "bridged alkyl," i.e., a bicyclic or polycyclic hydrocarbon group, for example, norbornyl, adamantyl, bicyclo[2.2.2]octyl, bicyclo [2.2.1]heptyl, bicyclo[3.2.1]octyl, or decahydronaphthyl. Alkyl groups optionally can be substituted, for example, with hydroxy (OH), halo, aryl, heteroaryl, ester, carboxylic acid, amide, guanidine, and amino.

As used herein, "cycloalkyl" refers to a specific alkyl group arranged in a cyclic structure. Examples of cycloalkyl groups include, but are not limited to, cyclopropyl, cyclobutyl, cyclopentyl, cyclohexyl, and cycloheptyl. "Heterocycloalkyl" refers to a cycloalkyl group containing one or more heteroatoms, e.g., N, O, and/or S.

As used herein, the terms "alkenyl" and "alkynyl" refer to groups similar to alkyl groups, but containing one or more double or triple bonds, respectively. The alkenyl or alkynyl group is optionally substituted with one or more substituent previously listed as an optional alkyl substituent.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, OCF$_3$, NO$_2$, CN, NC, OH, alkoxy, amino, CO$_2$H, CO$_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The substrates herein described can have asymmetric centers or axes. All chiral, diastereomeric, and racemic forms are included in the present invention. Many geometric isomers of olefins and the like also can be present in the compounds described herein, and all such stable isomers are contemplated in the present invention.

The methods disclosed herein preferably use a safety-catch linker on a solid support because of its stability during a variety of synthetic conditions. One specific safety catch linker comprises an acylsulfonamide, and has a formula of —$N(CH_2CN)SO_2(CH_2)_p$CONH-solid support, wherein p is an integer of 1 through 8. Other linkers that are stable to the reaction conditions of the disclosed methods also can be used. Examples of such linkers include thiopyrimidine linkers (Obrect, et al. *Helv. Chim. Acta,* 80:65-72 (1997)), safety catch acid labile linkers (Patek, et al., *Tetrahedron Lett.,* 32:3891-3894 (1991)), photocleavable safety catch linkers (Routledge, et al., *Tetrahedron Lett.,* 38:1227-1230 (1997)), and selenium safety catch linkers (Nicolaou, et al., *Chem. Eur. J.,* 7:3798-3823 (2001)).

The stability of the safety catch linker allows for a compound to be synthesized on the solid-support without concern that the compound, or the intermediates in the synthesis of the compound, remains bound to the solid support. The synthesized compound can then be removed from the solid support by N-alkylation of the linker, which results in a labile amide bond. The resulting labile amide bond then can be displaced by a nucleophile. Suitable nucleophiles include thiols, alcohols, amines, or carboxylates to form thioesters, esters, amides, or anhydrides, respectively. (See, e.g., Backes, et al., *J. Am. Chem. Soc.,* 118:3055-3056 (1996) and Backes, et al.,

*J. Org. Chem.,* 64:2322-2330 (1999).) Another suitable nucleophile can be a thioesterase, such as a serine residue of a Crp thioesterase, which can then assist in cyclization of a macrocycle, as disclosed herein.

Access of the thioesterase enzyme to the solid-support bound intermediate is needed in order to form the macrocyclic compounds disclosed herein. One exemplary means for providing suitable access of the enzyme to the support-bound intermediate is the use of a low-loading solid support. A low loading solid support is one which is capable of having up to about 0.5 mmol of a substrate per gram of support attached to its surface. (See, e.g., Meldal, *Tetrahedron Lett.,* 33:3077-3080 (1992) and Meldal, et al, *J. Chem. Soc. Chem. Commun.,* 1849-1850 (1994).) In some cases, the low loading solid support has a loading of about 0.01 to about 0.4 mmol/g, about 0.2 to about 0.35 mmol/g, or about 0.1 to about 0.3 mmol/g.

The solid support can be of polymer or glass substrate which is compatible with the reaction conditions of the disclosed methods. Suitable solid supports include, but are not limited to, polystyrene, Wang resin, Merrifield resin, polyethylene glycol, acrylamide, alkylated acylsulfonamide (safety catch) resin, and combinations thereof, such as co-polymers of any of the foregoing. One specific co-polymer contemplated is a polyethylene glycol-acrylaminde copolymer.

Compounds of formula (II) are prepared from compounds of formula (I) by the methods disclosed herein, as outlined in Scheme 2, below, wherein $X^1$ is selected from the group consisting of O, NH, and S; $X^4$ is selected from the group consisting of OH, $NH_2$, and SH; $X^{4'}$ is selected from the group consisting of O, NH, and S; $X^5$ is independently selected from the group consisting of O, S, NH, and $CR^6$; $R^2$ and $R^6$ are each independently selected from the group consisting of hydrogen and $C_{1-6}$alkyl; $R^1$, $R^3$, and $R^4$ are each independently selected from the group consisting of hydrogen, $C_{1-6}$alkyl, $C_{1-6}$alkylenearyl, $C_{1-6}$alkyleneheteroaryl, hydroxy$C_{1-6}$alkyl, thio$C_{1-6}$alkyl, $C_{1-6}$alkyleneCO$_2$H, $C_{1-6}$alkyleneNH$_2$, $C_{1-6}$alkyleneC(O)NH$_2$, and $C_{1-6}$alkyleneNH(NH)NH$_2$; $R^5$ is selected from the group consisting of aryl, heteroaryl, cycloalkyl, and heterocycloalkyl; a dashed line indicates an optional cis or trans double bond; Solid Support is a polymer or glass substrate; n is 1, 2, 3, 4, 5, 6, or 7; and m is 0 or 1.

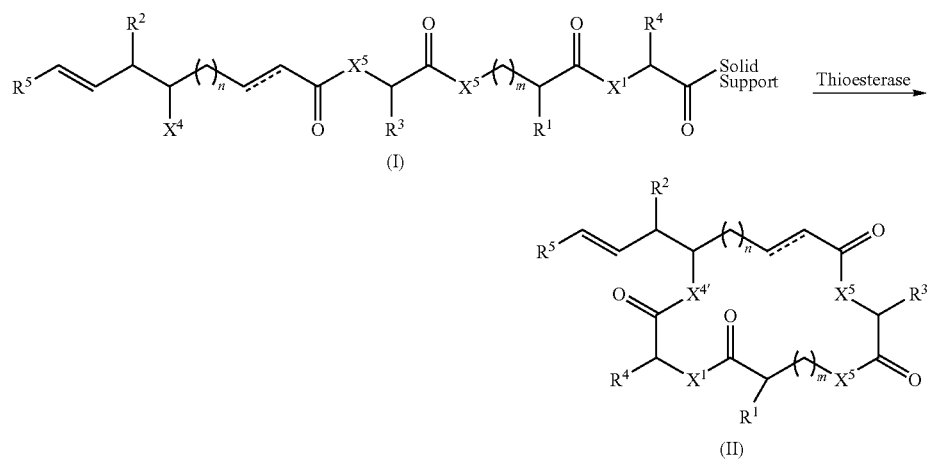

As used herein, the term "alkyl" refers to straight chained and branched hydrocarbon groups, nonlimiting examples of which include methyl, ethyl, and straight chain and branched propyl and butyl groups. Alkyl groups optionally can be substituted, for example, with hydroxy (OH), halo, aryl, heteroaryl, ester, carboxylic acid, amide, guanidine, and amino.

As used herein, the term "alkylene" refers to an alkyl group having a substituent. For example, the term "alkenylenearyl" refers to an alkyl group substituted with an aryl group. The alkylene group is optionally substituted with one or more substituent previously listed as an optional alkyl substituent.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, $OCF_3$, $NO_2$, CN, NC, OH, alkoxy, amino, $CO_2H$, $CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, $OCF_3$, $NO_2$, CN, NC, OH, alkoxy, amino, $CO_2H$, $CO_2$alkyl, aryl, and heteroaryl. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

The term "cycloalkyl" means a cyclic hydrocarbon group, e.g., cyclopropyl, cyclobutyl, cyclohexyl, or cyclopentyl.

"Heterocycloalkyl" is defined similarly as cycloalkyl, except the ring contains one to three heteroatoms independently selected from the group consisting of oxygen, nitrogen, and sulfur. Cycloalkyl and heterocycloalkyl groups can be saturated or partially unsaturated ring systems optionally substituted with, for example, one to three groups, independently selected from the group consisting of $C_{1-4}$alkyl, $C_{1-3}$alkyleneOH, $C(O)NH_2$, $NH_2$, oxo (=O), aryl, and OH. Heterocycloalkyl groups optionally can be further N-substituted with $C_{1-6}$alkyl, hydroxy$C_{1-6}$alkyl, $C_{1-3}$alkylenearyl, or $C_{1-3}$alkyleneheteroaryl.

The compound of formula (I) is contacted with a thioesterase to form the compound of formula (II). Suitable thioesterases include, but are not limited to, cryptophycin thioesterase, erythromycin thioesterase, pikromycin thioesterase, epothilone thioesterase, gramicidin thioesterase, surfactin thioesterase, bryostatin thioesterase, mycolactone thioesterase, rhizoxin thioesterase, tylosin thioesterase, nystatin thioesterase, FK506 thioesterase, tyrocidine thioesterase, daptomycin thioesterase, cyclosporin thioesterase, fengycin thioesterase, bacitracin thioesterase, pristinamycin thioesterase, kynurenine thioesterase, A54145 thioesterase, CDA thioesterase, friulimicin thioesterase, and mixtures thereof. In specific embodiments, the thioesterase comprises cryptophycin thioesterase (Crp TE).

The concentration of the thioesterase can be any amount sufficient to allow the formation of a compound of formula (II) or formula (IV). In some cases, the thioesterase is present in an amount of about 0.05 to about 0.5 µM, about 0.07 to about 0.4 µM, or about 0.1 to about 0.3 µM.

The reaction time of the process as outlined in Scheme 2 can be for about 5 minutes to about 48 hours. In some embodiments, the reaction time is about 1 hour to about 36 hours, about 2 hours to about 24 hours, or about 3 hours to about 12 hours.

Also disclosed herein is a process of preparing a compound of formula (IV) from a compound of formula (III) comprising admixing the compound of formula (III) with cryptophycin thioesterase to form the compound of formula (IV)

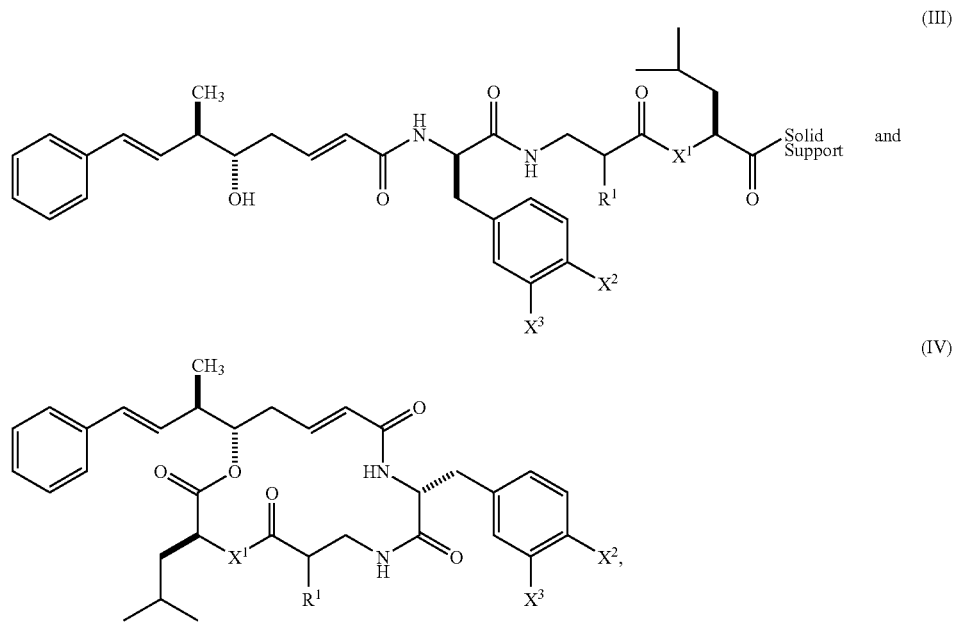

wherein $X^1$ is selected from the group consisting of O, NH, and S; $X^2$ is selected from the group consisting of hydrogen, $OC_{1-6}$alkyl, hydroxyl, and $C_{1-6}$alkyl; $X^3$ is selected from the group consisting of hydrogen, halo, and $C_{1-6}$alkyl; $R^1$ is selected from the group consisting of hydrogen, $C_{1-6}$alkyl, $C_{1-6}$alkylenearyl, $C_{1-6}$alkyleneheteroaryl, hydroxy$C_{1-6}$alkyl, thio$C_{1-6}$alkyl, $C_{1-6}$alkyleneCO$_2$H, $C_{1-6}$alkyleneNH$_2$, $C_{1-6}$alkyleneC(O)NH$_2$, and $C_{1-6}$alkyleneNH(NH)NH$_2$; and Solid Support is a polymer or glass substrate.

The methods disclosed herein result in a molar ratio of the compound of formula (IV) to the undesired byproduct compound of formula (V) of at least 2:1, and can be at least 3:1, or at least 4:1. Longer reaction times tends to produce more of the undesired compound of formula (V):

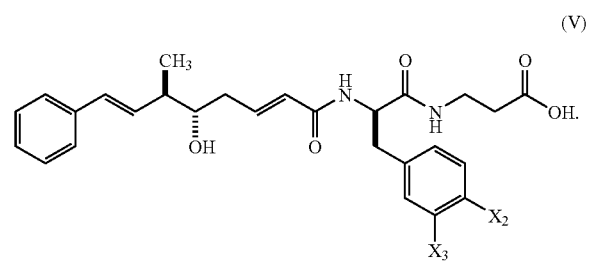

(V)

The compounds of formula (I) and of formula (III) can be prepared using known solid phase chemistry techniques. As outlined in Scheme 3, below, reagents having an acid functionality and a protected "$X^1$" functionality are reacted with the solid support, in this case 1, a solid support having a safety catch linker attached, to form an intermediate 2. The $X^1$ functional group can then be exposed by removal of the protecting group "PG" and subjecting the resulting compound to similar coupling conditions.

As used herein, the term "protecting group" refers to a chemical group that exhibits the following characteristics: (1) reacts selectively with the desired functionality in good yield to give a protected substrate that is stable to the projected reactions for which protection is desired; (2) is selectively removable from the protected substrate to yield the desired functionality; and (3) is removable in good yield by reagents compatible with the other functional group(s) generated in such protection reactions. Examples of protecting groups can be found in Greene et al., "Protective Groups in Organic Synthesis," 2d Ed. (John Wiley & Sons, Inc., New York, 1991). Selection of protecting groups and conditions to remove a protecting group is within the knowledge of the skilled artisan.

Any peptide coupling conditions can be used, including admixing the reagents (e.g., (1) protected acids and (2) free amine of the solid support or free amine or hydroxyl of the previously coupled moiety) in the presence of a coupling reagent. Coupling reagents include carbodiimides such as N,N'-dicyclohexylcarbodiimide (DCC), N,N'-diisopropyl-carbodiimide (DIC), 1-ethyl-3-(3'-dimethylaminopropyl) carbodiimide (EDCI), benzotriazoles 7-aza-1-hydroxybenzotriazole (HOAt), 1-hydroxybenzotriazole (HOBt), 6-chloro-1-hydroxybenzotriazole (Cl-HOBt), amininum and phosphonium based reagents such as N-[(dimethylamino)-1H-1,2,3-triazolo[4,5-b]pyridine-1-ylmethylene]-N-methylmethanaminium hexafluorophosphate N-oxide (HATU), N-[(1H-benzotriazol-1-yl)(dimethylamino)methylene]-N-methylmethanaminium hexafluorophosphate N-oxide (HBTU), N-[(1H-6-chlorobenzotriazol-1-yl)(dimethylamino)methylene]-N-methylmethan-aminium hexafluorophosphate N-oxide (HCTU), N-[(1H-benzotriazol-1-yl)(dimethylamino)methylene]-N-methylmethanaminium tetrafluoroborate N-oxide (TBTU), N-[(1H-6-chlorobenzot- Scheme 3

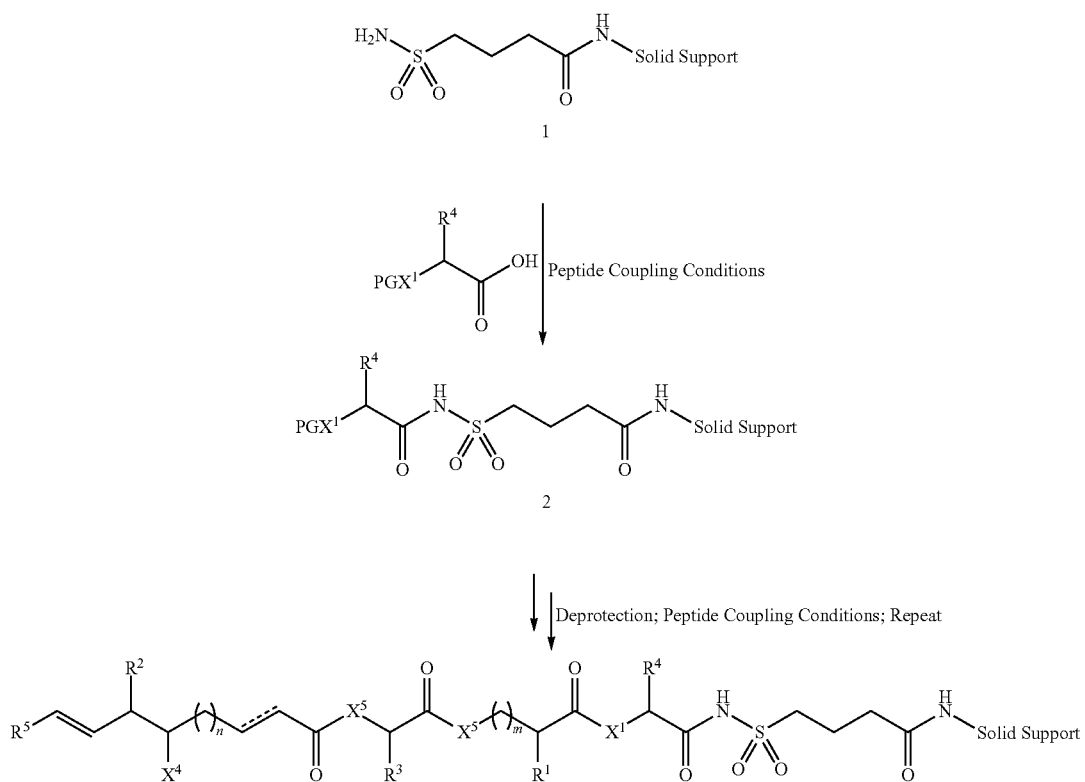

riazol-1-yl)(dimethylamino)methylene]-N-methylmethan-aminium tetrafluoroborate N-oxide (TCTU), 7-azabenzotriazol-1-yl-N-oxy-tris(pyrrolidino)phosphonium hexafluorophosphate (PyAOP) and benzotriazol-1-yl-N-oxy-tris(pyrrolidino)phosphonium hexafluorophosphate (Py-BOP).

EXAMPLES

The following examples are provided to illustrate the invention, but are not intended to limit the scope thereof.

All reactions were performed under nitrogen atmosphere. Fmoc-protected amino and hydroxy acids were either purchased from Bachem and Novabiochem (Fmoc-Leu-OH, Fmoc-β-Ala-OH, Fmoc-D-Phe-OH, Fmoc-D-Tyr(Me)-OH) or synthesized in a few steps starting from previously described compounds. 4-Sulfamylbutyryl AM PEGA resin was obtained from Novabiochem. Solvents were purchased from Fisher Scientific and freshly distilled before use ($CH_2Cl_2$, $CHCl_3$, THF, EtOAc, hexane, methanol, $Et_2O$) or obtained in Peptide Synthesis Grade (DMF, NMP). PyBOP, TBTU, HOBt, MSNT (1-(mesitylene-2-sulfonyl)-3-nitro-1H-1,2,4-triazole), DIPEA (diisopropyl-ethylamine), NMI (N-methylimidazole), DBU (1,8-diazabicyclo[5.4.0]undec-7-ene) and all other chemicals were obtained from Aldrich or Novabiochem and used directly.

$^1H$ and $^{13}C$ NMR spectra were recorded on a Varian Inova 400 MHz spectrometer. Proton chemical shifts are reported in ppm from an internal standard of residual chloroform (7.26 ppm), carbon chemical shifts are reported in ppm using an internal standard of residual chloroform (77.16 ppm). Proton chemical data are described as follows: chemical shift, multiplicity (s=singlet, d=doublet, t=triplet, q=quartet, m=multiplet, br=broad), coupling constant (in Hz) and integration. Mass spectra were recorded on a Micromass LCT time-of-flight mass spectrometer with electrospray ionization (ESI) mode. UV-VIS measurements were performed on a ABI SpectraMax M5 spectrophotometer. Analytical thin-layer chromatography (TLC) was performed on silica gel TLC aluminum sheets with a fluorescence indicator from EMD Chemicals. Visualization was accomplished with UV light (254 nm) and by dipping in a 20% solution of phosphomolybdic acid (PMA) in ethanol or in a $KMnO_4$ solution (3 g of $KMnO_4$, 20 g of $K_2CO_3$ and 0.25 g of NaOH in 300 mL of water) followed by heating. Expression and purification of cryptophycin thioesterase (Crp TE) was performed as reported in Beck, et al., *Biochemistry*, 44:13457-13466 (2005).

Three cryptophycin thioesterase substrates (3a-c) were synthesized on a polyethylene glycol-acrylamide copolymer resin modified with a safety catch linker: seco-desepoxyarenastatin, seco-cryptophycin-29 (seco-desepoxycryptophycin-21) and the seco form of an amide analog of arenastatin lacking the epoxy or methoxy moieties (Scheme 4).

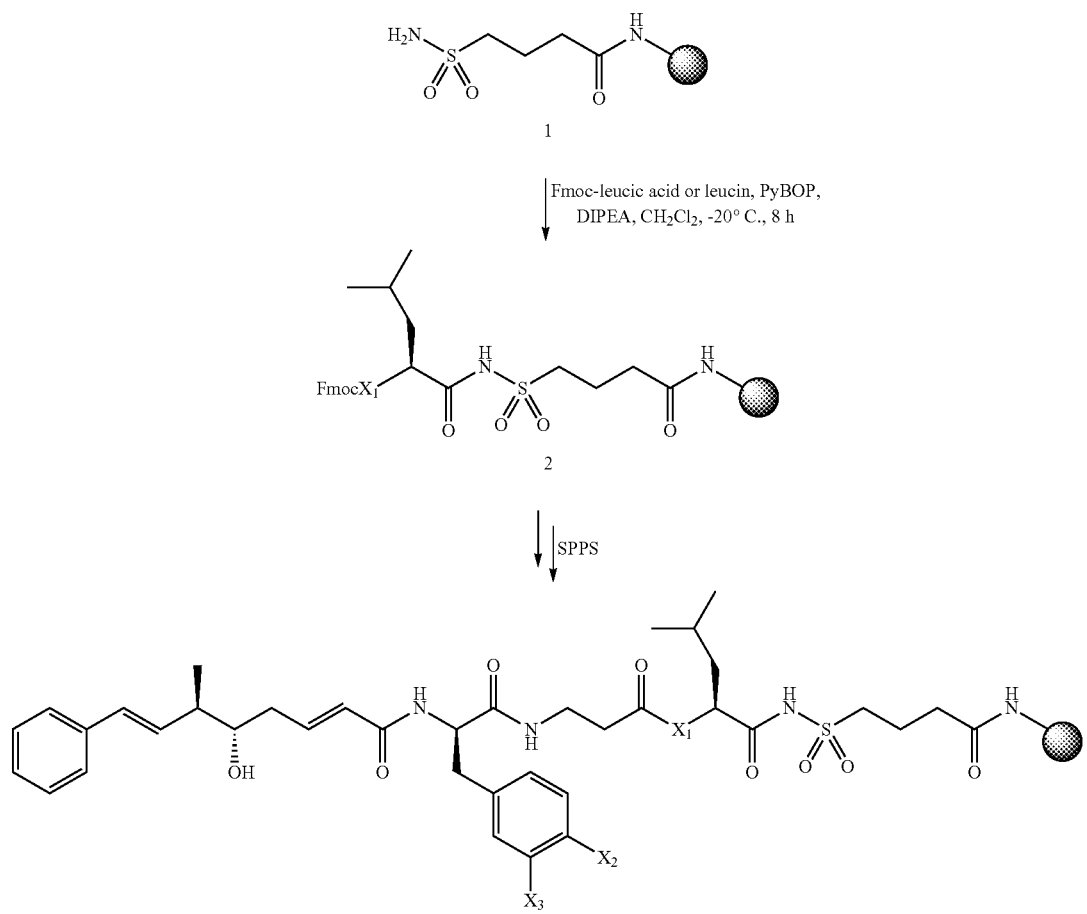

Scheme 4

Fmoc-protected leucic acid, leucine (unit D), β-alanine (unit C), O-methyl-D-tyrosine, 3-chloro-O-methyl-D-tyrosine and D-phenylalanine (unit B) were either commercially available or obtained in a few steps using known procedures. (See, Eissler, et al., *Synthesis*, 3747-3789 (2006) and Eggen, et al., *Med. Res. Rev.*, 22:85-101 (2002).) Polyketide unit A was synthesized according to Eggen et al., *J. Org. Chem.*, 65: 7792-7799 (2000). Attachment of unit D (L-leucic acid or leucine) to the commercial available 4-sulfamylbutyryl AM PEGA resin 1 was achieved using PyBOP in dichloromethane; peptide couplings were performed with TBTU; and the ester bond between units C and D was formed with MSNT (Scheme 4).

After alkylation of the acylsulfonamide linker with iodoacetonitrile, the activated resin (4a-c) was incubated with Crp TE in pH 8 phosphate buffer for 4 h. (See, Murakami, et al., *Tetrahedron*, 56:9121-9128 (2000) and Kotoku, et al., *Bioorg. Med. Chem.*, 14:7446-7457 (2006).) Extractive work-up yielded the cyclized compounds 5a-c and the corresponding seco-cryptophycins 6a-c as the only major cleaved products, as determined by HPLC (Scheme 5). The ratio of the desired cyclized product and undesired linear product varied from 4:1 to 2:1 for the different substrates. Longer incubation times with Crp TE (up to 24 h) led to an increased formation of the undesired linear products.

The substrates 3a-c on safety-catch PEGA resin (approx. 0.2 mmol) were washed with several portions of N-methyl pyrolidone (NMP). To the swollen resin were added NMP (5 mL), diisopropylethylamine (DIPEA) (11 eq) and iodoacetonitrile (25 eq), which was filtered through a plug of basic alumina prior to use. The reaction flask was shielded from light and agitated for 24 h at 35° C. The resin was washed sequentially with NMP (5×5 mL), dimethylformamide (DMF) (5×5 mL), water (5×5 mL) and pH 8 phosphate buffer (3×5 mL). Crp TE (3 mL, 60 μM in 25mM phosphate buffer, pH 8) was added, and the enzyme-resin mixture was left to stand for 4 h at 23° C. Next, the resin was washed with water (2×5 mL) and dichloromethane (5×5 mL). After extraction of the aqueous filtrate with dichloromethane, the combined organic extracts and filtrates were dried with $MgSO_4$, filtered and concentrated in-vacuo. Purification by flash-chromatography or RP-HPLC yielded the cryptophycins 5a-c and the seco-cryptophycins 6a-c. Cryptophycins 5a-c were obtained after separation by flash-chromatography or HPLC in milligram quantities (5 mg of 5a, 6 mg of 5b and 12 mg of 5c). The analytical data of compounds 5a and 5b proved to be identical with reported data. Significantly, amide analog 5c represents a new cryptophycin/arenastatin analog made accessible through this solid-phase chemoenzymatic approach.

Scheme 5

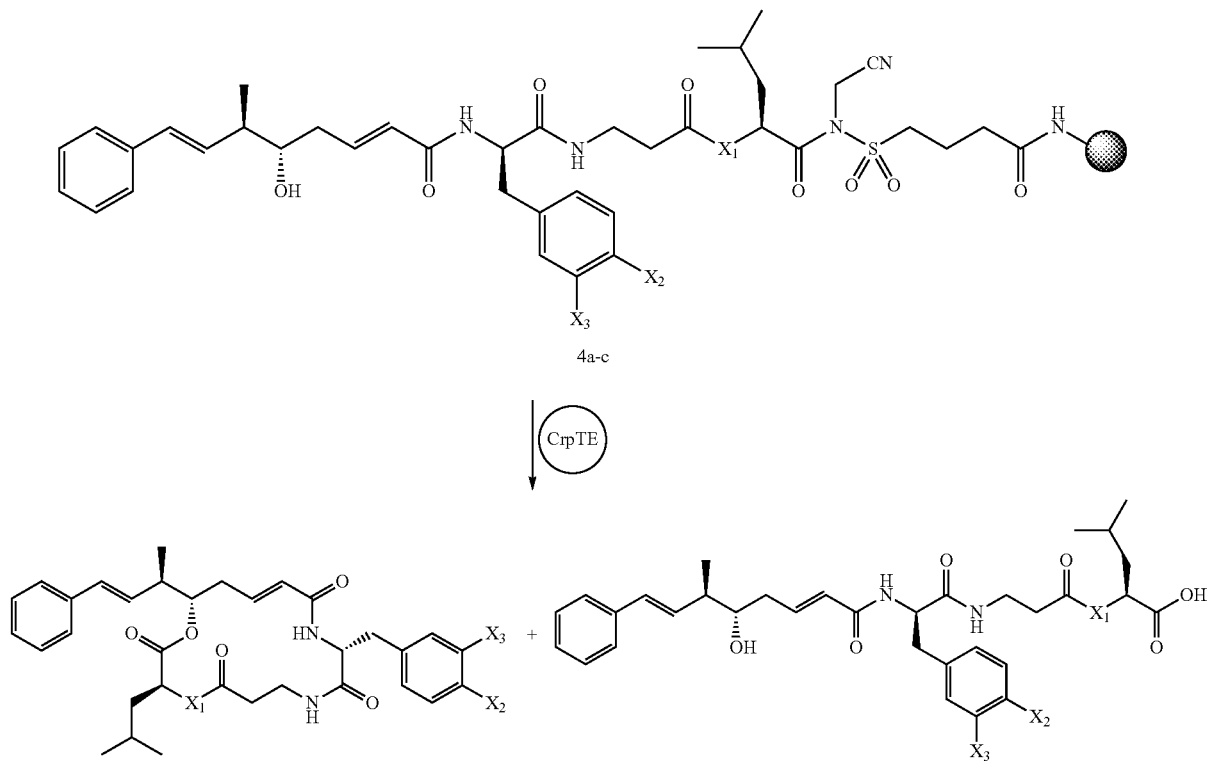

5a, $X_1$ = O, $X_2$ = OMe, $X_3$ = H (Desepoxyarenastatin)
5b, $X_1$ = O, $X_2$ = OMe, $X_3$ = Cl (Cryptophycin-29)
5c, $X_1$ = NH, $X_2$ = H, $X_3$ = H 6a, $X_1$ = O, $X_2$ = OMe, $X_3$ = H
6b, $X_1$ = O, $X_2$ = OMe, $X_3$ = Cl
6c, $X_1$ = NH, $X_2$ = H, $X_3$ = H In an additional experiment, the activated resin was incubated in pH 8 phosphate buffer without Crp TE. No cyclized products or seco-cryptophycins were observed using the same analytical techniques described above. Therefore, release and cyclization of cryptophycins from solid support are catalyzed by Crp TE. Formation of the seco-cryptophycins 6a-c is apparently mediated by a Crp TE catalyzed ring-opening of cryptophycins 5a-c or by a Crp TE catalyzed hydrolysis of the solid-phase bound substrates 4a-c, as previously observed.

Synthesis of Fmoc-protected leucic acid 7 and 3-chloro-O-methyl-D-tyrosine 8

(S)-2-(9'-Fluorenylmethoxycarbonyloxy)-4-methyl-pentanoic acid (7)

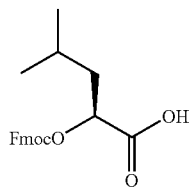

7

To a stirring solution of (S)-leucic acid benzyl ester (6.00 g, 27.0 mmol)[2] in pyridine (150 mL) was added 9-fluorenyl-methyl-chloroformate (8.38 g, 32.4 mmol). The reaction was stirred at 23° C. for 90 min, then concentrated in-vacuo. The residue was partitioned between $CH_2Cl_2$ and water, the organic layer was dried with $MgSO_4$, filtered and concentrated. Purification by flash chromatography (10% EtOAc/hexane) yielded a colorless oil that was dissolved in EtOAc (50 mL) and 10% Pd/C (50 mg) was added. The reaction mixture was stirred under $H_2$ for 40 h and subsequently filtered through a pad of celite. Evaporation of the solvent and chromatographic purification (20% EtOAc/hexane) afforded the title compound 7 (7.12 g, 74%) as colorless oil which solidified upon standing. TLC $R_f$=0.05 (20% EtOAc/hexanes, PMA stain); $^1$H NMR ($CDCl_3$, 400 MHz) δ 7.77 (d, J=7.5, 2H), 7.64 (t, J=7.5, 2H), 7.41 (t, J=7.5, 2H), 7.33 (d, J=7.5, 2H), 5.03 (dd, J=9.8, 3.9, 1H), 4.54 (dd, J=10.2, 7.0, 1H), 4.36 (dd, J=10.2, 7.8, 1H), 4.29-4.32 (m, 1H), 1.70-1.95 (m, 3H), 1.01 (d, J=6.5, 3H), 0.99 (d, J=6.5, 3H); $^{13}$C NMR ($CDCl_3$, 101 MHz) δ 176.3, 154.9, 143.5, 143.2, 141.4, 141.4, 128.1, 128.0, 127.4, 127.3, 125.4, 125.3, 120.2, 73.8, 70.5, 46.8, 39.7, 24.7, 23.1, 21.5; MS (ESI+) m/z 377.1 [M+Na]$^+$ ($C_{21}H_{22}NaO_5$ requires 377.1).

Fmoc-3-Cl-D-Tyr(Me)-OH (8)

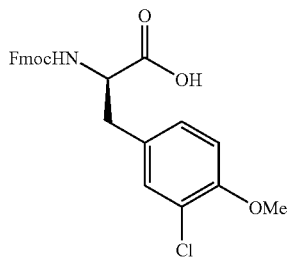

8

Boc-3-Cl-D-Tyr(Me)-OH (9.60 g, 29.1 mmol) was treated with 4 M HCl in dioxane (25 mL) at 23° C. for 1 h then the reaction mixture was concentrated in vacuo. The residual white solid was dissolved in 10% aqueous $Na_2CO_3$ (60 mL), dioxane (60 mL) and N-(9-Fluorenylmethoxy-carbonyloxy) succinimide (9.82 g, 29.1 mmol) were added. The reaction mixture was stirred at 23° C. for 18 h, then diluted with water (100 mL). The aqueous phase was extracted with $Et_2O$ (2×100 mL), acidified to pH 2 (conc. HCl) and extracted with EtOAc (3×100 mL). The combined EtOAc phases were washed with saturated aqueous NaCl, dried with $MgSO_4$, filtered and concentrated. Without further purification the title compound 8 (12.65 g, 96%) was obtained as white foam. TLC $R_f$=0.26 (EtOAc, PMA stain); $^1$H NMR ($CDCl_3$, 400 MHz) δ 9.82 (br s, 1H), 7.76 (d, J=7.6, 2H), 7.56 (t, J=7.6, 2H), 7.39 (t, J=7.6, 2H), 7.31 (d, J=7.6, 2H), 7.19 (d, J=1.6, 1H), 6.99 (dd, J=8.3, 1.6, 1H), 6.80 (d, J=8.3, 1H), 5.44 (d, J=7.8, 1H), 4.64-4.69 (m, 1H), 4.46 (dd, J=10.5, 7.0, 1H), 4.35 (dd, J=10.5, 7.0, 1H), 4.21 (t, J=7.0, 1H), 3.83 (s, 3H), 3.14 (dd, J=14.1, 5.3, 1H), 3.02 (dd, J=14.1, 6.3, 1H); $^{13}$C NMR ($CDCl_3$, 101 MHz) δ 175.0, 155.9, 154.2, 143.7, 141.4, 131.1, 128.8, 128.8, 127.8, 127.2, 125.2, 125.1, 120.1, 112.2, 67.2, 56.1, 54.6, 47.2, 36.8; MS (ESI+) m/z 474.1 [M+Na]$^+$ ($C_{25}H_{22}ClNNaO_5$ requires 474.1).

Synthesis of Cryptophycin Unit A (9)

Cryptophycin unit A, hydroxy group protected as TBS ether and carboxylic acid as tert-butyl ester, was synthesized according to the publication by Eggen et al, *J. Org. Chem.*, 65:7792-7799 (2000). Removal of both protecting groups in one step was accomplished as described below.

(2E, 5S, 6R, 7E)-5-Hydroxy-6-methyl-8-phenylocta-2,7-dienoic acid (9)

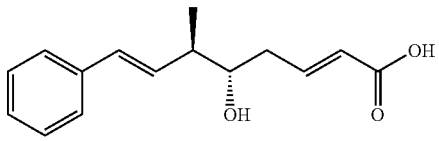

9 tert-Butyl (2E, 5S, 6R, 7E)-5-[(tert-butyl-dimethylsilyl)-oxy]-6-methyl-8-phenyl-octa-2,7-dienoate (725 mg, 1.74 mmol) was dissolved in $CH_2Cl_2$ (8 mL) and trifluoroacetic acid (2 mL). The solution was stirred at 23° C. for 4 h then concentrated in-vacuo. Residual trifluoroacetic acid was removed by coevaporation with toluene. Flash chromatography (2% MeOH/$CH_2Cl_2$+1% AcOH) afforded the title compound 9 (210 mg, 49%) as pale yellow oil. TLC $R_f$=0.24 (2% MeOH/$CH_2Cl_2$+1% AcOH, $KMnO_4$ stain); $^1$H NMR ($CDCl_3$, 400 MHz) δ 7.23-7.39 (m, 5H), 7.16 (dt, J=15.6, 7.4, 1H), 6.49 (d, J=15.8, 1H), 6.13 (dd, J=15.8, 8.7, 1H), 5.94 (dt, J=15.6, 1.4, 1H), 3.68 (ddd, J=7.9, 6.0, 3.9, 1H), 2.50-2.56 (m, 1H), 2.36-2.44 (m, 2H), 1.16 (d, J=6.8, 3H); $^{13}$C NMR ($CDCl_3$, 101 MHz) δ 171.0, 148.5, 137.0, 132.4, 130.9, 128.8, 127.7, 126.4, 122.9, 73.9, 43.6, 37.5, 17.0; MS (ESI+) m/z 269.1 [M+Na]$^+$ ($C_{15}H_{18}NaO_3$ requires 269.1).

Synthesis of Linear Cryptophycin Thioesterase Substrates 3a-c on Solid Support Attachment of first amino or hydroxy acid: In a typical experiment, 4-sulfamylbutyryl AM PEGA resin (1 g, 0.28 mmol) was washed with $CH_2Cl_2$ and cooled to $-20°$ C. Fmoc-leucic acid 7 (397 mg, 1.12 mmol) or Fmoc-Leu-OH (396 mg, 1.12 mmol) and PyBOP (583 mg, 1.12 mmol), dissolved in $CH_2Cl_2$ (5 mL), and DIPEA (0.39 mL, 2.24 mmol) were added. The reaction mixture was left to stand at $-20°$ C. for 8 h with occasional shaking and subsequently filtered and washed with $CH_2Cl_2$. The coupling procedure was repeated once to obtain resin with a loading value of 0.20-0.25 mmol/g.

General methods for solid-phase synthesis: The Fmoc deprotection and the formation of peptide bonds were performed as follows. To the above prepared resin (0.25 mmol) was added a solution of 2% piperidine and 2% DBU in DMF (5 mL), shaken for 10 min, filtered and washed with DMF. The deprotection procedure was repeated twice. After thoroughly washing with DMF, the resin was agitated with a solution of the Fmoc-protected amino acid (0.75 mmol), TBTU (0.75 mmol) and HOBt (0.75 mmol) in DMF (5 mL) and with DIPEA (1.50 mmol) for 30 min. The resin was filtered, washed with DMF and the coupling was repeated once. With a negative Kaiser test, the synthesis proceeded to the next round of deprotection and coupling. At last, cryptophycin unit A 9 (2×0.30 mmol) was coupled in the same way as the Fmoc-protected amino acids.

Ester bond formation on solid support: To form the ester bond between β-alanine and leucic acid on solid support, Fmoc-leucic acid loaded resin (0.25 mmol) was washed with DMF and the alcohol was deprotected with a solution of 2% piperidine and 2% DBU in DMF (5 mL) for 10 min. The deprotection procedure was repeated twice and the resin was subsequently washed with DMF and $CH_2Cl_2$. Fmoc-β-Ala-OH (233 mg, 0.75 mmol), dissolved in THF (3 mL), $CH_2Cl_2$ (3 mL), MSNT (222 mg, 0.75 mmol) and NMI (44 μL, 0.56 mmol) were added and the reaction mixture was agitated for 1 h, then washed with THF and $CH_2Cl_2$. The esterification was repeated twice to obtain a loading value of 0.18 mmol/g.

Purification and Characterization of Cryptophycins 5a-c and Seco-cryptophycins 6a-c The cleaved cryptophycins 5a-c and seco-cryptophycins 6a-c from solid support were either separated by flash chromatography (5% $MeOH/CH_2Cl_2$) or by using reverse phase HPLC with a 10 to 100% gradient of acetonitrile in 0.1% TFA/water over the course of 40 min on an Alltech Econosil 10 μm C18 column (250 mm×4.6 mm). The products were analyzed by $^1H$ NMR spectroscopy and/or by ESI-TOF mass spectrometry in the positive ion mode.

Desepoxyarenastatin (5a): Yield after purification (FC): 5 mg (8.5 μmol) of a white solid; $^1H$ NMR ($CDCl_3/d^4$-MeOH, 400 MHz) δ 7.04-7.22 (m, 5H), 7.00 (d, J=8.6, 2H), 6.67 (d, J=8.6, 2H), 6.54 (ddd, J=16.4, 10.8, 4.6, 1H), 6.28 (d, J=15.8, 1H), 5.88 (dd, J=15.8, 8.9, 1H), 5.66 (d, J=16.4, 1H), 4.87-4.92 (m, 1H), 4.80 (dd, J=9.8, 3.5, 1H), 4.46-4.51 (m, 1H), 3.64 (s, 3H), 3.30-3.34 (m, 1H), 3.20-3.24 (m, 1H), 3.03 (dd, J=14.5, 5.7, 1H), 2.72 (dd, J=14.5, 8.8, 1H), 2.41-2.44 (m, 3H), 2.16-2.25 (m, 2H), 1.43-1.65 (m, 3H), 1.01 (d, J=6.8, 3H), 0.60 (d, J=6.2, 3H), 0.56 (d, J=6.4, 3H); MS (ESI+) m/z 591.3 $[M+H]^+$ ($C_{34}H_{43}N_2O_7$ requires 591.3).

Cryptophycin-29 (5b): Yield after purification (HPLC): 6 mg (9.6 μmol) of a white solid; $^1H$ NMR ($CDCl_3$, 400 MHz) δ 7.18-7.33 (m, 6H), 7.08 (br t, 1H), 7.06 (dd, J=8.4, 2.0, 1H), 6.81 (d, J=8.4, 1H), 6.66 (ddd, J=15.2, 10.4, 5.2, 1H), 6.47 (d, J=8.4, 1H), 6.39 (d, J=15.8, 1H), 5.98 (dd, J=15.8, 8.8, 1H), 5.74 (d, J=15.2, 1H), 4.98-5.02 (m, 1H), 4.89 (dd, J=10.0, 3.3, 1H), 4.64-4.69 (m, 1H), 3.83 (s, 3H), 3.55-3.63 (m, 1H), 3.28-3.35 (m, 1H), 3.13 (dd, J=14.3, 6.2, 1H), 2.87 (dd, J=14.3, 8.0, 1H), 2.50-2.58 (m, 3H), 2.26-2.34 (m, 2H), 1.55-1.63 (m, 3H), 1.11 (d, J=6.8, 3H), 0.72 (d, J=6.3, 3H), 0.68 (d, J=6.3, 3H); MS (ESI+) m/z 625.3 $[M+H]^+$ ($C_{34}H_{42}ClN_2O_7$ requires 625.3).

Amide analog (5c): Yield after purification (HPLC): 12 mg (21 μmol) of a white solid; $^1H$ NMR ($CDCl_3/d^4$-MeOH, 400 MHz) δ 7.10-7.24 (m, 10H), 6.56 (ddd, J=15.2, 11.2, 4.1, 1H), 6.32 (d, J=15.8, 1H), 5.93 (dd, J=15.8, 8.8, 1H), 5.69 (dd, J=15.2, 1.5, 1H) 4.96-5.01 (m, 1H), 4.51-4.55 (m, 1H), 4.35 (dd, J=8.8, 6.2, 1H), 4.54-3.60 (m, 1H), 3.14-3.23 (m, 2H), 2.76 (dd, J=14.4, 10.1, 1H), 2.44-2.48 (m, 1H), 2.22-2.30 (m, 4H), 1.24-1.52 (m, 3H), 1.05 (d, J=6.8, 3H), 0.65 (d, J=6.4, 3H), 0.64 (d, J=6.5, 3H); MS (ESI+) m/z 560.3 $[M+H]^+$ ($C_{33}H_{42}N_3O_5$ requires 560.3).

seco-Desepoxyarenastatin (6a): MS (ESI+) m/z 609.4 $[M+H]^+$ ($C_{34}H_{45}N_2O_8$ requires 609.3). seco-Cryptophycin-29 (6b): MS (ESI+) m/z 643.3 $[M+H]^+$ ($C_{34}H_{44}ClN_2O_8$ requires 643.3). seco-Amide analog (6c): MS (ESI+) m/z 578.4 $[M+H]^+$ ($C_{33}H_{44}N_3O_6$ requires 578.3).

Additional features and variations of the invention will be apparent to those skilled in the art from the entirety of this application, including the detailed description, and all such features are intended as aspects of the invention. Likewise, features of the invention described herein can be re-combined into additional embodiments that also are intended as aspects of the invention, irrespective of whether the combination of features is specifically mentioned above as an aspect or embodiment of the invention. Also, only such limitations which are described herein as critical to the invention should be viewed as such; variations of the invention lacking limitations which have not been described herein as critical are intended as aspects of the invention.

What is claimed:

1. A process of preparing a compound of formula (II) comprising
    admixing a compound of formula (I) and a thioesterase to form the compound of formula (II),

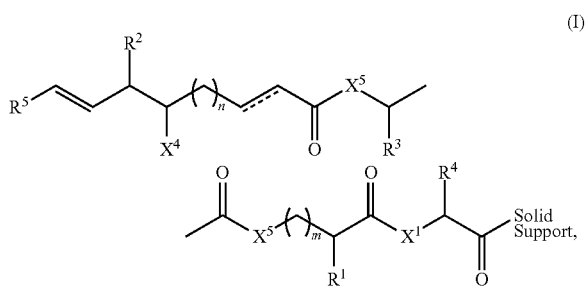

-continued (II)

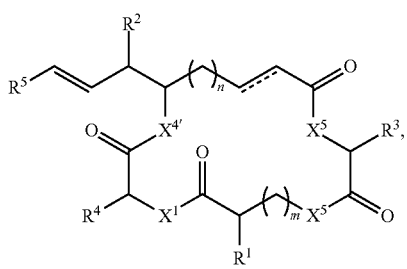

wherein $X^1$ is selected from the group consisting of O, NH, and S; $X^{4'}$ is selected from the group consisting of OH, $NH_2$, and SH; $X^4$ is selected from the group consisting of O, NH, and S; $X^5$ is independently selected from the group consisting of O, S, NH, and $CR^6$; $R^2$ and $R^6$ are each independently selected from the group consisting of hydrogen and $C_{1-6}$alkyl; $R^1$, $R^3$, and $R^4$ are each independently selected from the group consisting of hydrogen, $C_{1-6}$alkyl, $C_{1-6}$alkylenearyl, $C_{1-6}$alkyleneheteroaryl, hydroxy$C_{1-6}$alkyl, thio$C_{1-6}$alkyl, $C_{1-6}$alkyleneCO$_2$H, $C_{1-6}$alkyleneNH$_2$, $C_{1-6}$alkyleneC(O)NH$_2$, and $C_{1-6}$alkyleneNH(NH)NH$_2$; $R^5$ is selected from the group consisting of aryl, heteroaryl, cycloalkyl, and heterocycloalkyl; a dashed line indicates an optional cis or trans double bond; Solid Support comprises a polymer or glass substrate; n is 1, 2, 3, 4, 5, 6, or 7; and m is 0 or 1.

2. The process of claim 1, wherein the thioesterase is selected from the group consisting of cryptophycin thioesterase, erythromycin thioesterase, pikromycin thioesterase, epothilone thioesterase, gramicidin thioesterase, surfactin thioesterase, bryostatin thioesterase, mycolactone thioesterase, rhizoxin thioesterase, tylosin thioesterase, nystatin thioesterase, FK506 thioesterase, tyrocidine thioesterase, daptomycin thioesterase, cyclosporin thioesterase, fengycin thioesterase, bacitracin thioesterase, pristinamycin thioesterase, kynurenine thioesterase, A54145 thioesterase, CDA thioesterase, friulimicin thioesterase, and mixtures thereof.

3. The process of claim 1, wherein $R^3$ is $C_{1-6}$alkylenearyl, and aryl is selected from the group consisting of phenyl, 4-hydroxy-3-chlorophenyl, and 4-hydroxyphenyl.

4. The process of claim 1, wherein $R^5$ is aryl or heteroaryl.

5. The process of claim 1, wherein the polymer substrate comprises a polyethylene glycol-acrylamide copolymer.

6. The method of claim 5, wherein the polymer substrate further comprises an alkylated acylsulfonamide linker.

7. A process of preparing a compound of formula (IV), comprising
admixing a compound of formula (III) and a cryptophycin thioesterase to form a compound of formula (IV):

(III)

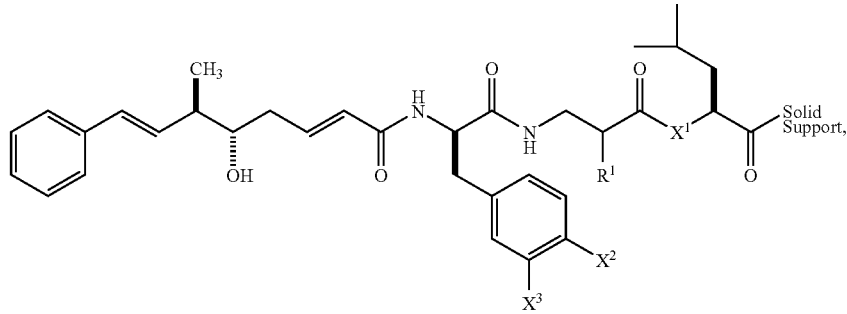

(IV)

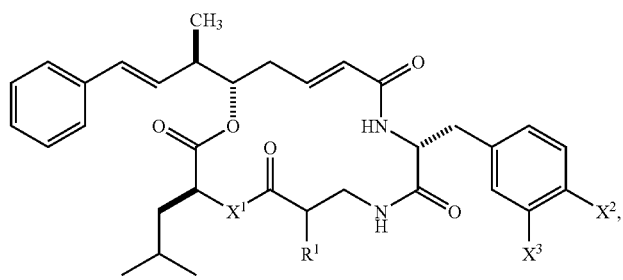

wherein $X^1$ is selected from the group consisting of O, NH, and S; $X^2$ is selected from the group consisting of hydrogen, OC$_{1-6}$alkyl, hydroxyl, and $C_{1-6}$alkyl; $X^3$ is selected from the group consisting of hydrogen, halo, and $C_{1-6}$alkyl; $R^1$ is selected from the group consisting of hydrogen, $C_{1-6}$alkyl, $C_{1-6}$alkylenearyl, $C_{1-6}$alkyleneheteroaryl, hydroxy$C_{1-6}$alkyl, thio$C_{1-6}$alkyl, $C_{1-6}$alkyleneCO$_2$H, $C_{1-6}$alkyleneNH$_2$, $C_{1-6}$alkyleneC(O)NH$_2$, and $C_{1-6}$alkyleneNH(NH)NH$_2$; and Solid Support comprises a polymeric or glass substrate.

8. The process of claim 7, wherein the cryptophycin thioesterase has a concentration of about 0.1 μmol to about 0.3 μmol.

9. The process of claim 7, wherein the molar ratio of the compound of formula (IV) to a byproduct compound of formula (V) is at least 2:1,

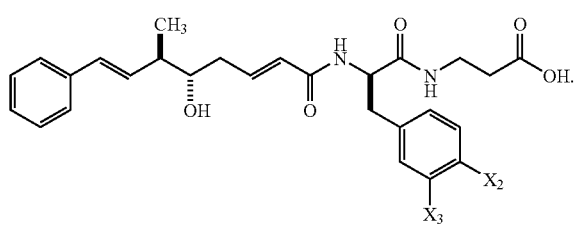

(V)

10. The process of claim 1, wherein the thioesterase is cryptophycin thioesterase.

11. The process of claim 7, wherein the polymeric substrate has a loading of about 0.15 to about 0.3 mmol/g.

12. The process of claim 7, wherein the polymeric substrate comprises a polyethylene glycol-acrylamide copolymer.

13. The process of claim 12, wherein the polymeric substrate further comprises an alkylated acylsulfonamide linker.

14. The process of claim 13, wherein the alkylated acylsulfonamide comprises a formula —N(CH$_2$CN)SO$_2$(CH$_2$)$_p$CONH-polymer substrate, wherein p is 1, 2, 3, 4, 5, 6, 7, or 8.

* * * * *